(12) United States Patent
Sixto, Jr. et al.

(10) Patent No.: US 8,226,655 B1
(45) Date of Patent: Jul. 24, 2012

(54) DISTRACTION ASSEMBLY

(76) Inventors: Robert Sixto, Jr., Miami, FL (US); Juergen Andrew Kortenbach, Miami Springs, FL (US)

( * ) Notice: Subject to any disclaimer, the term of this patent is extended or adjusted under 35 U.S.C. 154(b) by 625 days.

(21) Appl. No.: 11/825,324

(22) Filed: Jul. 5, 2007

(51) Int. Cl.
*A61B 17/60* (2006.01)

(52) U.S. Cl. ........................................ 606/86 R; 606/58

(58) Field of Classification Search ...... 433/7, 172–176; 600/235, 237–239, 242, 606, 70–71, 280–299, 600/902–906; 606/57–58, 86 R, 70–71, 606/280–299, 902–906
See application file for complete search history.

(56) References Cited

U.S. PATENT DOCUMENTS

| | | | |
|---|---|---|---|
| 3,800,420 A * | 4/1974 | Ouaknine | 433/7 |
| 5,439,377 A * | 8/1995 | Milanovich | 433/7 |
| 5,575,790 A | 11/1996 | Chen et al. | |
| 5,626,581 A | 5/1997 | Staehlin et al. | |
| 5,766,004 A | 6/1998 | Besselink et al. | |
| 5,951,288 A | 9/1999 | Sawa | |
| 5,976,142 A | 11/1999 | Chin | |
| 5,980,252 A * | 11/1999 | Samchukov et al. | 433/215 |
| 6,033,412 A | 3/2000 | Losken et al. | |
| 6,050,819 A * | 4/2000 | Robinson | 433/173 |
| 6,113,599 A * | 9/2000 | Landsberger | 606/60 |
| 6,126,662 A | 10/2000 | Carmichael et al. | |
| 6,171,313 B1 * | 1/2001 | Razdolsky et al. | 606/86 R |
| 6,200,324 B1 | 3/2001 | Regni, Jr. | |
| 6,280,191 B1 | 8/2001 | Gordon | |
| 6,309,220 B1 | 10/2001 | Gittleman | |
| 6,616,672 B1 * | 9/2003 | Essiger | 606/105 |
| 6,706,042 B2 * | 3/2004 | Taylor | 606/57 |
| 7,331,781 B1 * | 2/2008 | Bandeen | 433/7 |
| 7,384,265 B2 * | 6/2008 | Hanks | 433/7 |
| 2003/0055433 A1 * | 3/2003 | Krenkel et al. | 606/86 |
| 2005/0130092 A1 * | 6/2005 | Minoretti et al. | 433/7 |
| 2005/0159755 A1 * | 7/2005 | Odrich | 606/86 |
| 2006/0144169 A1 * | 7/2006 | Porat et al. | 73/864.14 |

* cited by examiner

*Primary Examiner* — Thomas C. Barrett
*Assistant Examiner* — Larry E Waggle, Jr.
(74) *Attorney, Agent, or Firm* — Malloy & Malloy, P.L.

(57) ABSTRACT

A distraction assembly for automatically facilitating bone growth which may be required for the application of a dental implant is presented. A drive assembly is dimensioned and configured to be anchored within the mouth of a patient and includes a drive component and a timing assembly collectively disposed and structured to drive at least one displacement member along a predetermined path of travel, wherein the displacement member is connected to a bone segment associated with the implant site. The drive component and timing assembly are further cooperatively structured and disposed to cause incremental advancement of said displacement member along the predetermined path of travel and concurrent displacement of the bone segment relative to the implant site at a constant or otherwise predetermined rate.

23 Claims, 17 Drawing Sheets

DISTRACTION ASSEMBLY

BACKGROUND OF THE INVENTION

1. Field of the Invention

This invention is directed to a distraction assembly structured to automatically facilitate bone growth which may be required for the application of a dental implant. A drive assembly is dimensioned and configured to be anchored within the mouth of a patient and structured to incrementally advance at least one displacement member and a bone segment attached thereto such that sufficient bone growth will be generated at a preferred rate to support the dental implant.

2. Description of the Related Art

Modern day dentistry has advanced to the point that dental implants are commonly utilized for the replacement of missing, natural teeth. However, in many instances bone loss at the implant site is such that the application of a dental implant without further dental procedures is not possible. Bone loss is frequently the result of injury or the natural process of reabsorption to the extent that the implant site has been damaged or otherwise configured in an undesirable fashion. Accordingly, a procedure generally known as bone distraction could benefit a patient especially when a dental implant is being applied at a specific or predetermined implant site that is lacking in sufficient bone mass.

More specifically, the requirements for a successful implantation typically involve sufficient native bone to allow the installation of a dental implant and further to allow the osteointegration of the implant. Every tooth that is lost by accidental means, through tooth decay and/or the natural aging process, presents a distinctly unique set of constraints that will determine the likelihood of success for artificial tooth implantation.

Although each instance requiring the implantation of a tooth is unique, applicable situations can be grouped generally into two major categories. One is implantation of the molars and the other is implantation of the incisor or canine teeth. In the case of molars, which typically amount to the majority of instances where implantation is desirable, significant absorption of bone commonly results in difficulty in implanting artificial teeth. Current means for mitigating the risk of a failed implant involve the use of bone filler, or bone transplantation. Both are costly and involve a high level of expertise to assure the desired outcome.

The technology associated with bone distraction is known and conventionally involves the use of some type of mechanical means periodically and manually adjusted to assure that the growth of the bone at a predetermined implant site continues until the desired increase in bone mass is achieved. One problem and/or disadvantage associated with conventional or known bone distraction techniques also involves a certain dependency on the patient to provide the necessary input that will result in the periodic separation of the corresponding bone fragments associated with the implant site. Moreover, utilizing conventional techniques frequently results in too much separation of the bone fragment which in turn results in the growth of soft tissue at the implant site. Such generated soft tissue grows more readily and has a tendency to disrupt the formation of the required bone mass. In turn, too little separation of the associated bone segments results in the bone solidifying and the necessity of terminating the distraction process. This problem is further exacerbated by the digital nature of the current distraction process. More specifically, existing procedures involve a process which is mostly "static", wherein such a static condition is violently disrupted by a sudden movement or disruption of the bone fragment in the range of generally one millimeter.

Accordingly, while known or conventional techniques and procedures associated with bone distraction for purposes of the application of a dental implant may be functional in accomplishing increased bone mass at the implant site, significant disadvantages and problems are generally associated therewith. Therefore, there is a need in the dental profession and in particular with the procedure and techniques associated with bone distraction for a proposed system, method, apparatus and associated techniques that effectively "automate" the bone distraction procedure. More specifically, the automation of bone separation at the implant site, resulting in sufficient bone growth over time, would overcome many if not all of the significant problems and disadvantages associated with known or conventional bone distraction technology.

More specifically, a proposed distraction assembly would preferably involve a drive assembly, which includes both a drive component and a timing assembly cooperatively disposed and structured to control the displacement of the bone fragment associated with the implant site over a predetermined period of time. By way of example, the period of time associated with an automated bone distraction technique could possibly be less than thirty days depending on the amount of bone mass that is required to accomplish a successful dental implant. Further by way of example, a proposed automated distraction assembly could be operatively structured to accomplish displacement approximately in the range of 0.5 mm to 1 mm per day until the desired distraction is created. With this method and the associated proposed automated distraction assembly, a distraction of 3 mm could take place any where from three days to six days.

In addition, an improved and proposed automated distraction assembly could provide movement of the bone fragments associated with the implant site throughout the entire period of bone distraction. Such a technique and associated structure would overcome the bone being in a static condition for an extended period of time thereby facilitating bone growth and eliminating or significantly reducing the possibility of the bone solidifying. Further, the provision of a timing assembly in the preferred and proposed automated distraction assembly will be operable to allow a delayed beginning of the period over which bone distraction is intended to occur. This could be accomplished so that the initial insult response that is typical of an injury is triggered at a predetermined time to start the bone regeneration process.

An additional feature associated with the timing assembly and its structural and interactive operation with the drive component of the drive assembly, is the ability to determine and regulate the maximum displacement per day of the bone segment(s) at the implant site to a desired range of preferably 1 mm. The degree of movement would be subject to a minimum amount that does not allow the solidification of the bone. It is, of course, understood that the rate of the separation of the bone fragments associated with the implant site may determine the quality of bone that is regenerated.

SUMMARY OF THE INVENTION

The present invention is directed to a distraction assembly structured to automatically facilitate bone growth or regeneration sufficient to facilitate the application of a dental implant at a predetermined implant site. Accordingly, the various preferred embodiments of the present invention overcome many of the significant disadvantages and problems associated with known and/or conventional techniques and procedures commonly utilized for the regeneration of bone mass at a dental implant site.

One feature of the present invention is the incremental displacement of a bone segment(s) within predetermined ranges and at a predetermined, preferably constant rate of displacement. As such, the present invention is distinguishable from known and conventional bone distraction procedures which apply a manual, disruptive adjustment of the bone fragment at the implant site which in turn may require input from the end user. Moreover, problems and disadvantages associated with excessive separation of the bone fragment, resulting in growth of soft tissue and attendant disruption of bone formation, would be overcome. Similarly, conventional distraction procedures resulting in too little separation and the attendant solidification of the bone would also be overcome by virtue of the automated operative function of each of the preferred embodiments of the bone distraction assembly of the present invention.

More specifically, the distraction assembly of the present invention automatically facilitates bone growth to a degree sufficient to apply an intended dental implant at the distraction site. Accordingly, the distraction assembly comprises a drive assembly which is dimensioned and configured to be placed in operative relation to the dental implant site within the mouth of the patient. Further, the drive assembly and other operative components associated therewith may remain in the mouth of the patient, for the relatively extended period of time necessary to accomplish the regeneration of sufficient bone mass. Proper anchoring and/or securement of the drive assembly is accomplished by a support frame which is anchored to corresponding bone tissue associated with the implant site. The support frame is formed from a material which is autoclavable or which can be sterilized in other fashions such as using gamma and ETO techniques. In addition at the end of the distraction process, the support frame can remain in place within the mouth of the patient in substantially overlying but protectively spaced relation to the implant site while the drive assembly and other operative components are removed. The remaining presence of the support frame serves to ensure that the normal eating and drinking habits of the patient does not compromise the distraction that has been accomplished. By way of example, the support frame can be disposed and remain in a protective, operative position to protect the distractive bone while the bone solidifies and reaches the required strength. Such a range of occupancy of the support frame within the patient's mouth can extend from generally one to three months.

Further, each of the preferred embodiments of the present invention comprises a drive assembly, as set forth above, which is connected in driving relation to at least one displacement element. In turn, the displacement element is secured, in an appropriate manner, to a bone segment associated directly with the implant site. The opposite end or other appropriate portion of the displacement member is interconnected to the drive assembly so as to be forced along a predetermined path of travel which serves to appropriately displace the attached bone segment incrementally over a predetermined period of time and within predetermined displacement ranges. Further by way of example, current operational characteristics facilitate a displacement range of approximately 1 mm per day until the desired bone mass growth has been accomplished. It is emphasized that the specific degree of distraction may vary dependent on the quantity of bone mass required to accomplish an effective and secure dental implant. Accordingly, common to each of the preferred embodiments of the distraction assembly of the present invention are structural and operative features of the drive assembly and cooperative components associated therewith to accomplish an incremental advancement of the displacement member along a predetermined path of travel. As such, displacement of the bone segment, relative to the implant site, occurs at a predetermined rate and most preferably at a substantially constant rate.

Further, the preferred embodiments of the distraction assembly of the present invention include the aforementioned drive assembly comprising a drive component cooperatively structured and interactively operable with a timing assembly. The timing assembly would effectively regulate the drive component, at least to the extent of accomplishing the aforementioned incremental advancement of the displacement member as it is forced along a predetermined path by operation the drive component. As also set forth above, the operative features of the timing assembly in cooperation with the driving force generated by the drive component will result in the displacement of the bone segment incrementally and concurrently relative to the implant site. The timing assembly is cooperatively structured with the drive component to accomplish the incremental displacement of the bone segment, secured to the displacement member over a predetermined rate and preferably at a constant rate.

Therefore, one preferred embodiment of the present invention comprises a drive assembly wherein the drive component comprises an electronically powered drive motor. The drive motor may be powered by sufficiently sized batteries wherein electric current flow to the electric drive motor is regulated by a timing assembly in the form of an electronic control. The electronic control may comprise appropriate electronic circuitry which regulates current flow in the manner intended, such that activating pulses of current flow are delivered to the electric drive motor. As a result, a drive force is periodically generated to accomplish the aforementioned and preferred incremental advancement of the displacement member and concurrent incremental displacement of the bone segment attached to and movable with displacement member. Accordingly, the electronic control serving to control flow of current to the drive components serves as the aforementioned timing assembly. As will be more apparent hereinafter, both the drive component and the associated timing assembly may vary in both structure and function dependent on which of the plurality of preferred embodiments are utilized.

Accordingly, another preferred embodiment of the subject distraction assembly comprises a drive assembly which includes a drive component in the form of a biasing assembly. The biasing assembly may take a variety of different forms such as, but not limited to, a torsion spring structured to generate a substantially continuous biasing force when activated. In cooperation therewith, this additional preferred embodiment includes a timing assembly in the form of a timing member interconnected to and cooperatively structured with the drive component or biasing assembly so as to restrict movement thereof. Such restricted movement of the biasing assembly or drive component is such as to determine the incremental advancement of the displacement member driven by the biasing assembly. Furthermore, this preferred embodiment of distraction assembly may be considered to be "self contained" in the sense that no external source of energy or power need be directed thereto, such as in the embodiment of the present invention, wherein the drive component comprises an electric motor.

Additional structural and operative features of this self contained drive assembly are associated with the structure and operation of the timing assembly. More specifically, the timing assembly is preferably formed of a material demonstrating predetermined "creep" characteristics. Such creep characteristics are predetermined to be sufficient to regulate and thereby determine the incremental movement of the biasing assembly and in turn the incremental advancement of the displacement member and secured bone segment driven thereby. In the science of materials, the term "creep" is used to describe the tendency of the material to move or deform permanently to relieve an applied stress. More specifically, such material deformation occurs as a result of long exposure to levels of stress that are below the yield or ultimate strength of the material. The rate of creep or deformation of the material in question is generally considered to be a function of the material properties, the exposure time to the stress, the temperature and the applied load or degree of stress itself. Accordingly, depending on the magnitude of the applied stress and its duration, the amount and rate of deformation or "creep characteristics" of a material may be predetermined. Many materials demonstrate predetermined creep characteristics including metals such as lead and many polymers.

In terms of this preferred embodiment of the distraction assembly of the present invention the timing member is formed of a material demonstrating sufficient and/or anticipatory creep characteristics when a determinable stress is applied thereto. Moreover, due to placement in the patient's mouth, the material of which the timing member is formed is subjected to a relatively constant temperature of 98.6° F. As practically applied, the stress applied to the timing member is the biasing force generated by the biasing assembly defining the drive component which also can be predetermined or anticipated. Therefore, the self contained drive assembly of this preferred embodiment of the present invention can be structured and operative to accomplish an incremental advancement of the driven displacement member, which in turn results in a concurrent, incremental displacement of the bone segment associated with the implant site at a predetermined and preferably constant rate.

Other features associated with each of the plurality of preferred embodiments of the distraction assembly of the present invention include a dimension and configuration of the drive assembly sufficient for prolonged occupancy of the patient's mouth. Further, the cooperative structuring of the aforementioned support frame is such as to dispose the drive assembly on the buccal side of the bone tissue in which the implant side is located. Further, structural features associated with the support assembly itself serve to anchor a distal portion of the support frame on the lingual side of the bone tissue as well as the opposite, buccal side of the bone tissue. As such, a secure mounting and support of the drive assembly and operative components associated therewith is established. Further, the driving or forced movement of the displacement member along a predetermined path of travel is assured by the secured anchoring of the drive assembly and support frame, wherein the predetermined path of travel of the displacement member as it incrementally advances may vary dependent upon the particular preferred embodiment utilized and applied. As will be explained in greater detail hereinafter, the configurations of the different paths of travel of the displacement member may include a substantially or at least partially arcuate configuration and/or a substantially and at least partially linear or laterally directed path of travel, again dependent upon the specific preferred embodiment of the distraction assembly utilized.

Therefore, the distraction assembly of the present invention overcomes many of the disadvantages and problems associated with conventional or known techniques and procedures associated with bone distraction. More specifically, the distraction assembly of the present invention includes structural and operative features which automate bone growth specifically, but not exclusively, for the application of a dental implant at an implant site which can be applied at various locations and utilized to implant various teeth of the patient, as will be set forth in greater detail hereinafter.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
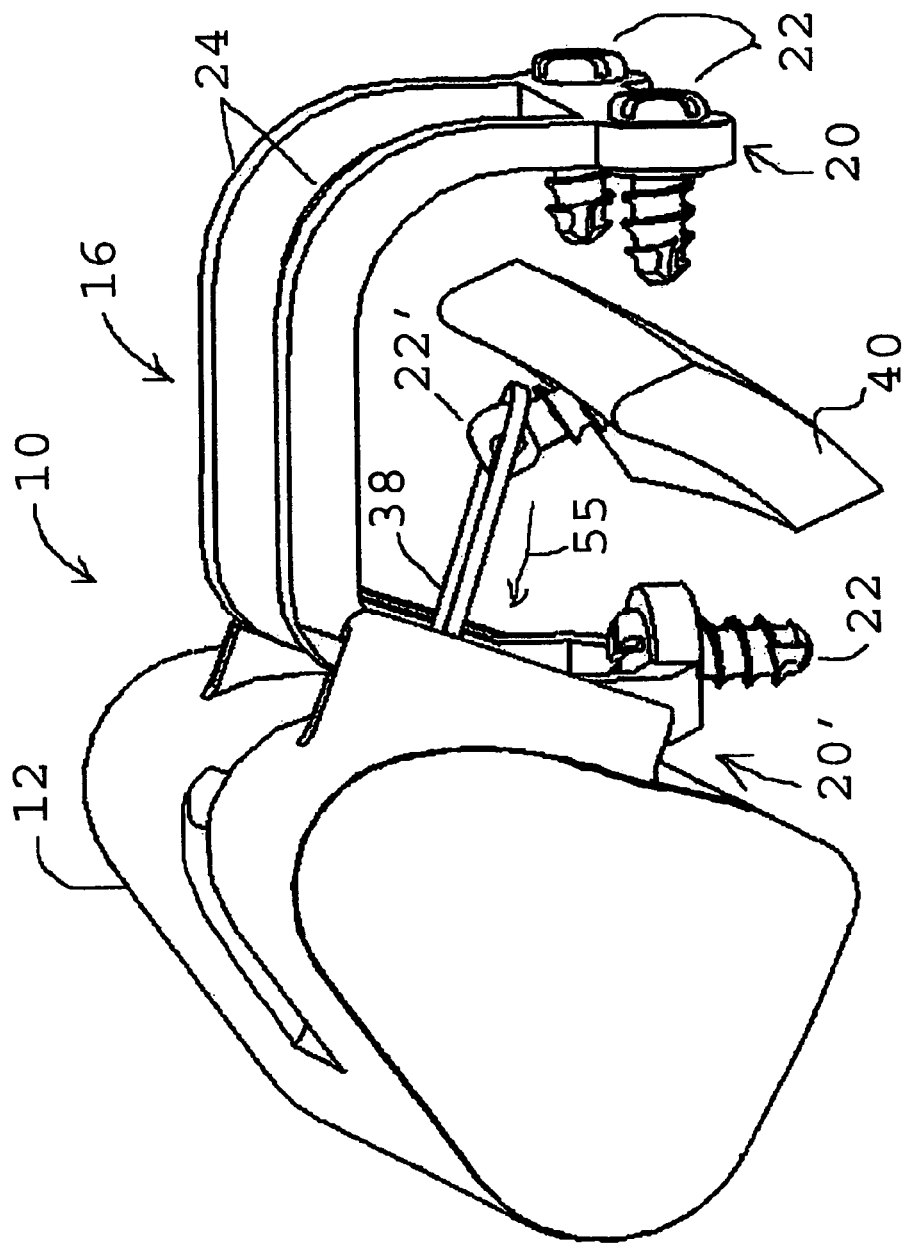
FIG. 1 is a perspective view of one preferred embodiment of the distraction assembly of the present invention attached to a bone segment intended to be displaced from an associated implant site but otherwise unattached to the implant site.
Figure 2:
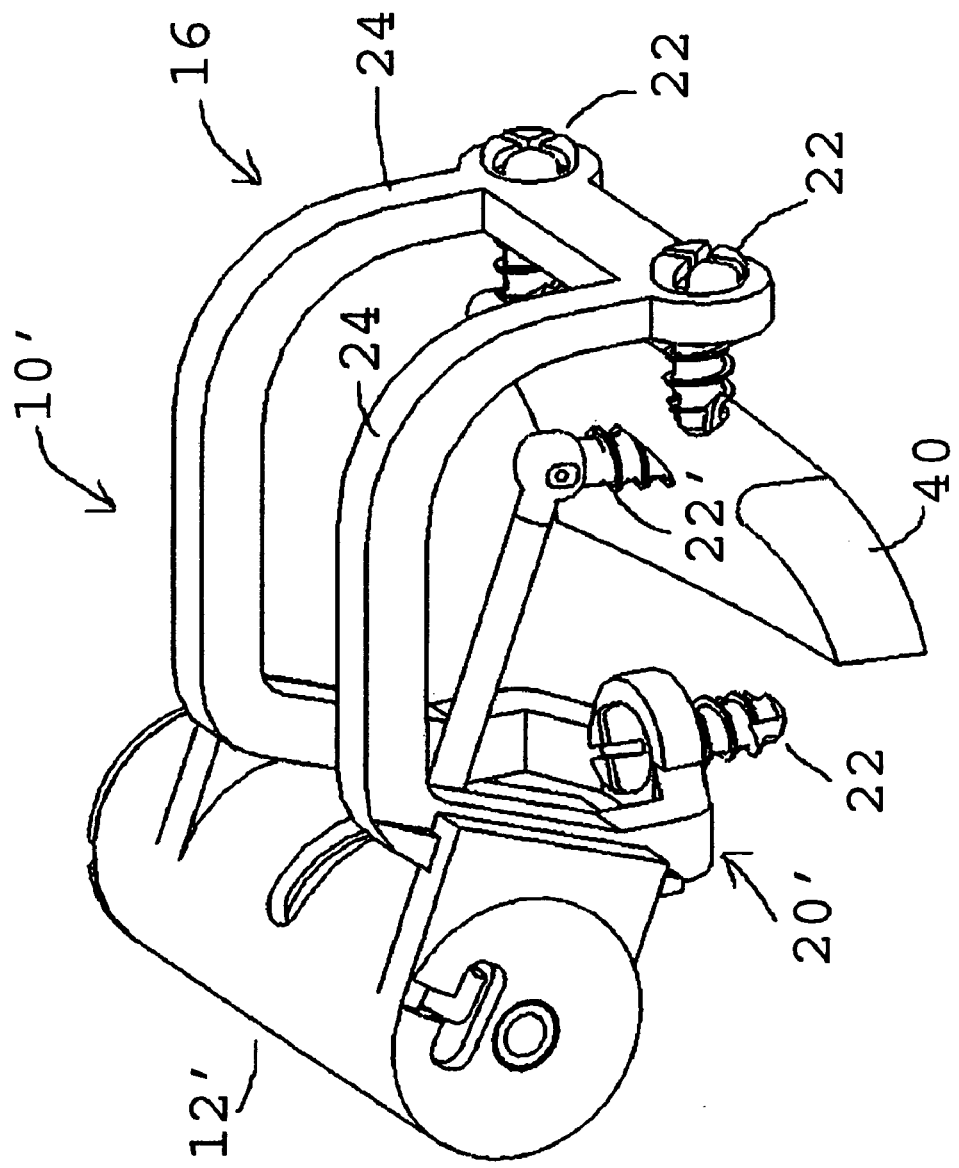
FIG. 2 is another preferred embodiment of the distraction assembly of the present invention also connected to a corresponding bone segment but otherwise being unattached or mounted adjacent the implant site.
Figure 3:
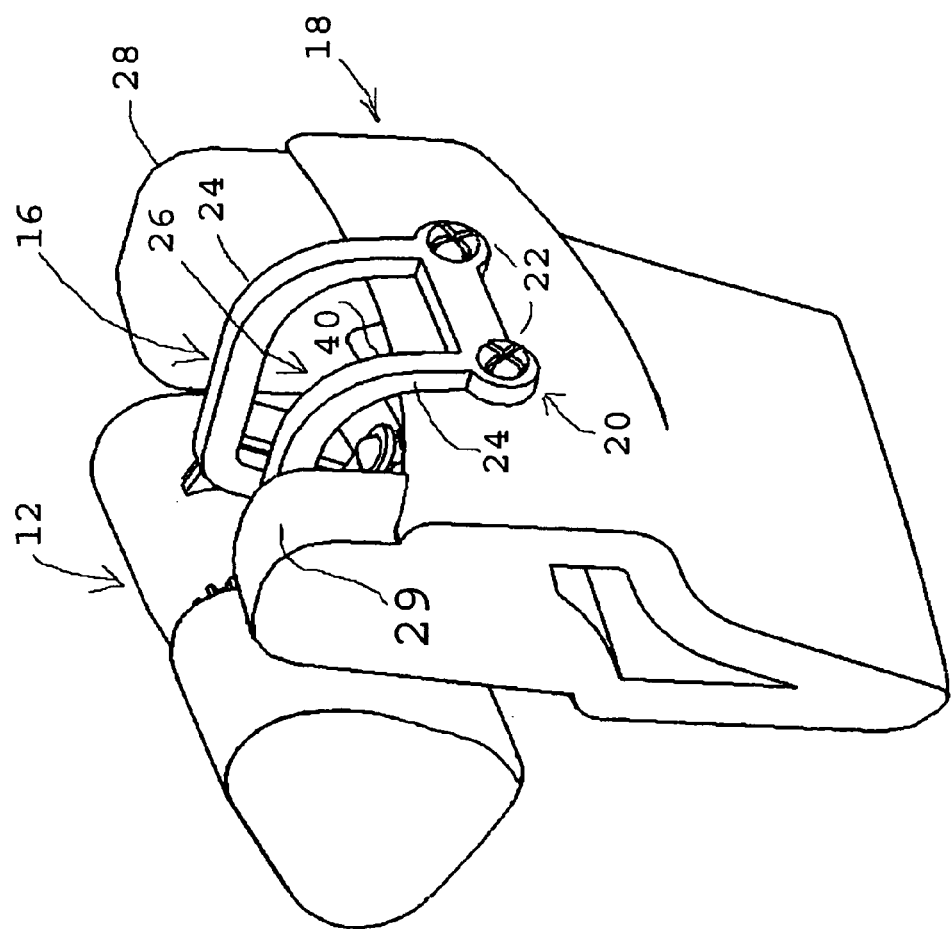
FIG. 3 is a rear perspective view of the embodiment of FIG. 1 anchored in an operative position to corresponding bone tissue and operatively disposed relative to an implant site.
Figure 4:
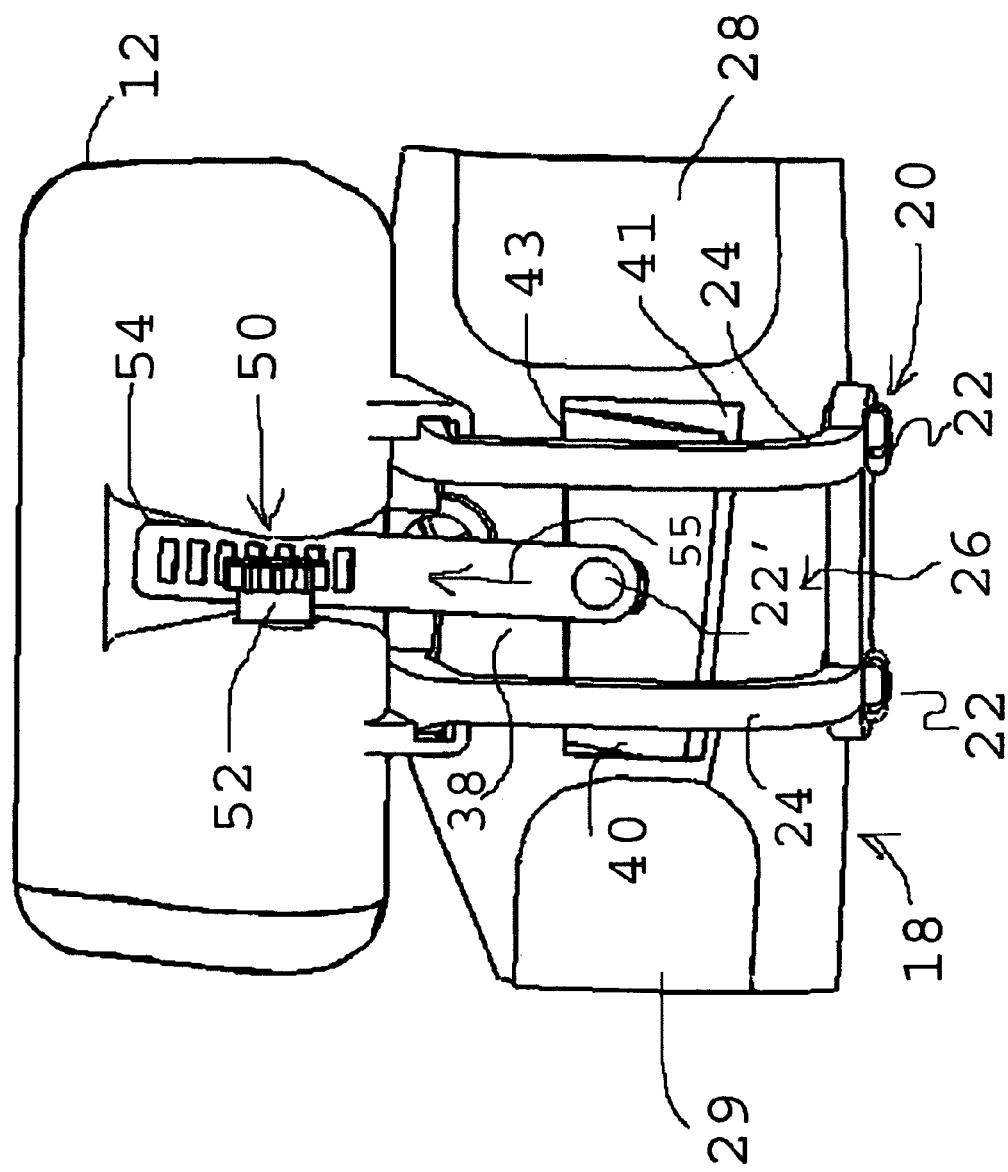
FIG. 4 is a top view of the embodiment of FIG. 3.
Figure 16:
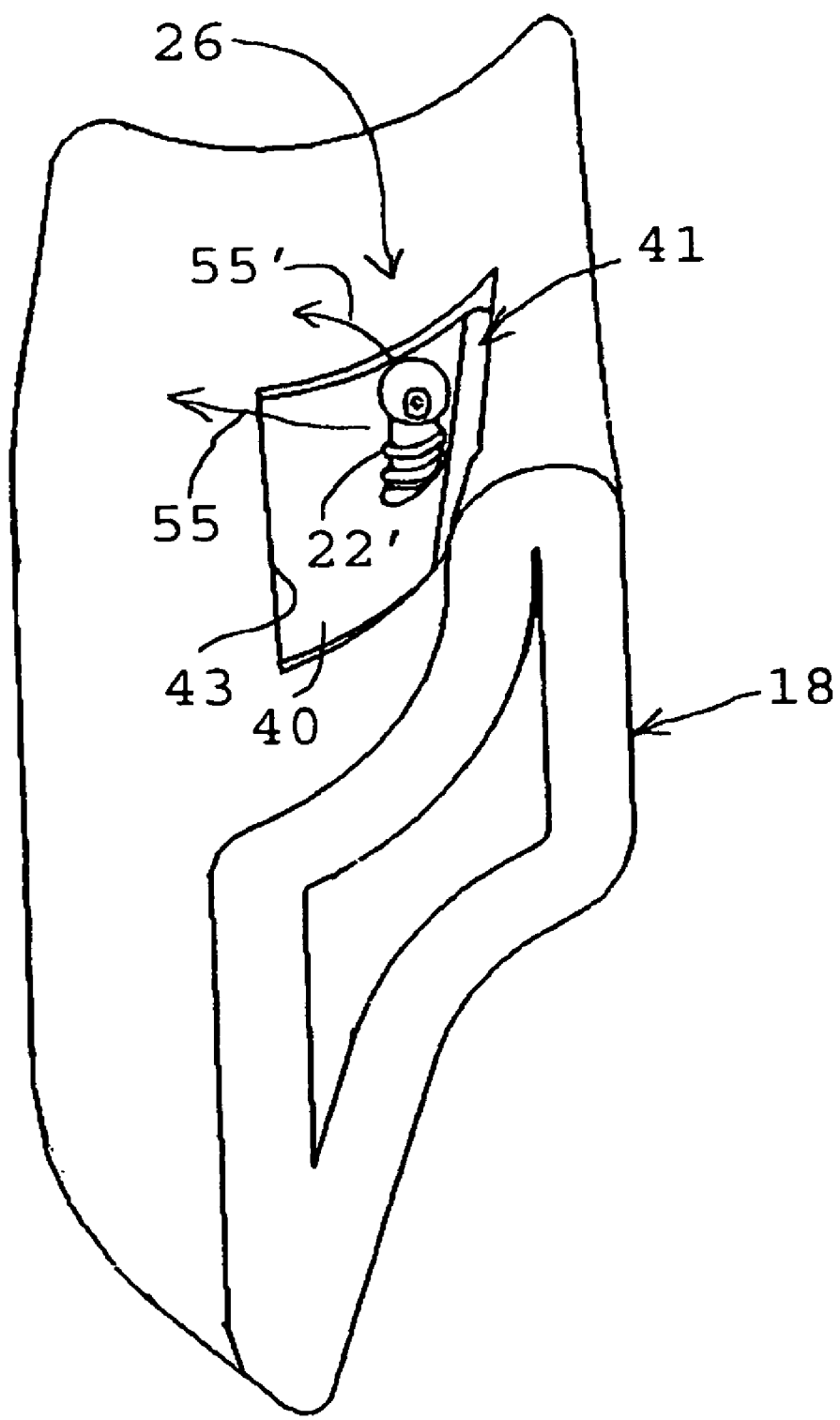
FIGS. 16 and 17 are perspective views in schematic form indicating the path of travel and incremental displacement of a bone segment located at an implant site and distinguishable by utilization of the preferred embodiment of FIG. 1 or the preferred embodiment of FIG. 2.
Figure 17:
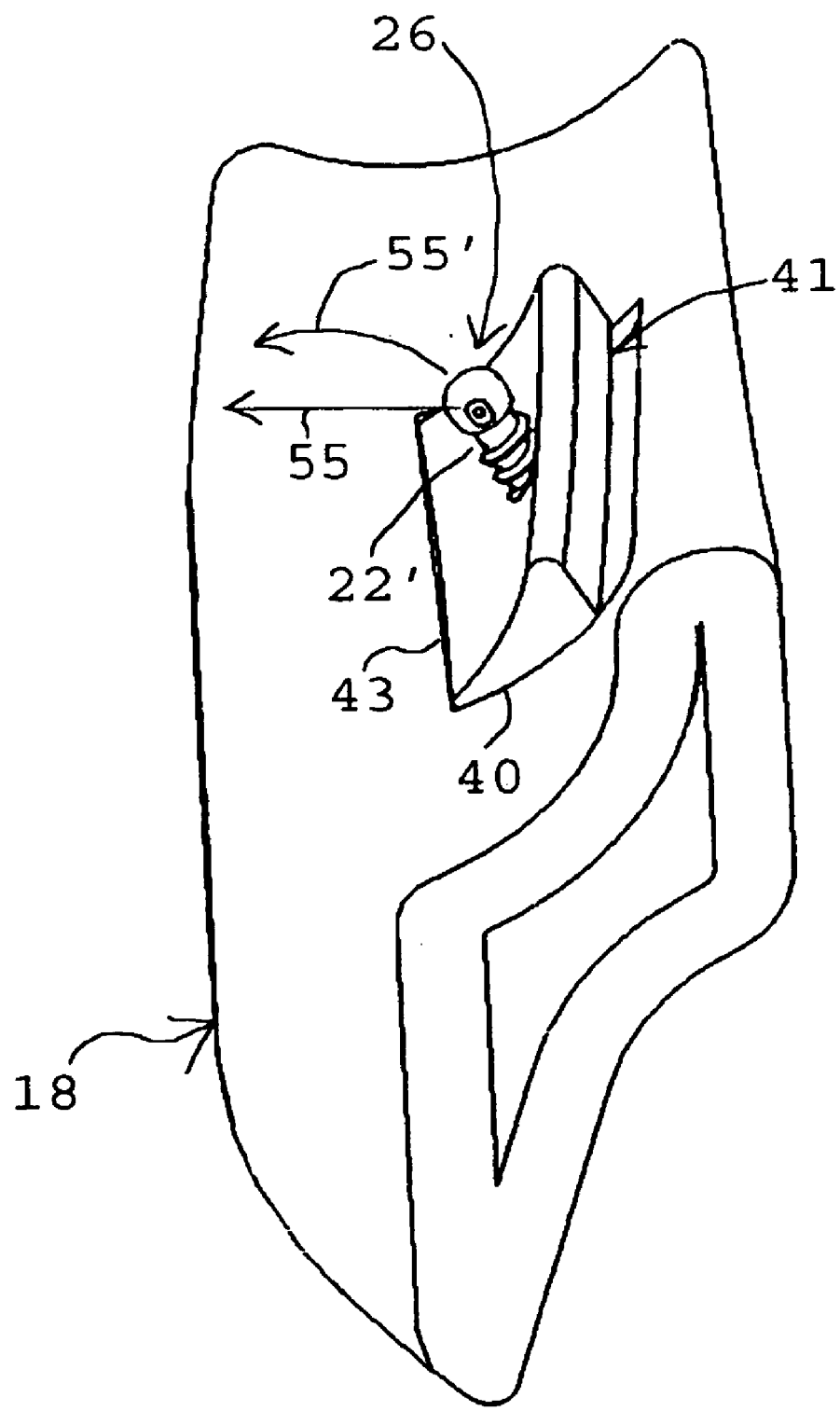

As represented in the accompanying drawings, the present invention is directed to a distraction assembly, wherein one preferred embodiment thereof is generally represented as 10 in FIG. 1 and yet another preferred embodiment is generally indicated as 10' in FIG. 2. Moreover, additional structural and operative features of the preferred embodiment of FIG. 1 are represented in detail in the accompanying FIGS. 3-7. Similarly, additional structural and operative features of the distraction assembly 10' are represented in detail in FIG. 8 through 12. Also, FIGS. 16 and 17 are schematic representations provided for the purpose of clarity, which are generic to both the embodiments of FIGS. 1 and 2 and are included as demonstrating similar but distinguishing operative characteristics of the two preferred embodiments, as set forth in greater detail hereinafter.

As will also be apparent, each of the preferred embodiments of the distraction assembly 10 and 10' includes structural and operative features which facilitate bone growth, in an automated manner, sufficient to apply a dental implant at a preferred implant site. As such, incremental displacement of a bone segment, associated with the implant site, is accomplished at a predetermined and preferably constant rate of displacement in order to most efficiently facilitate the growth or regeneration of bone mass.

Figure 5:
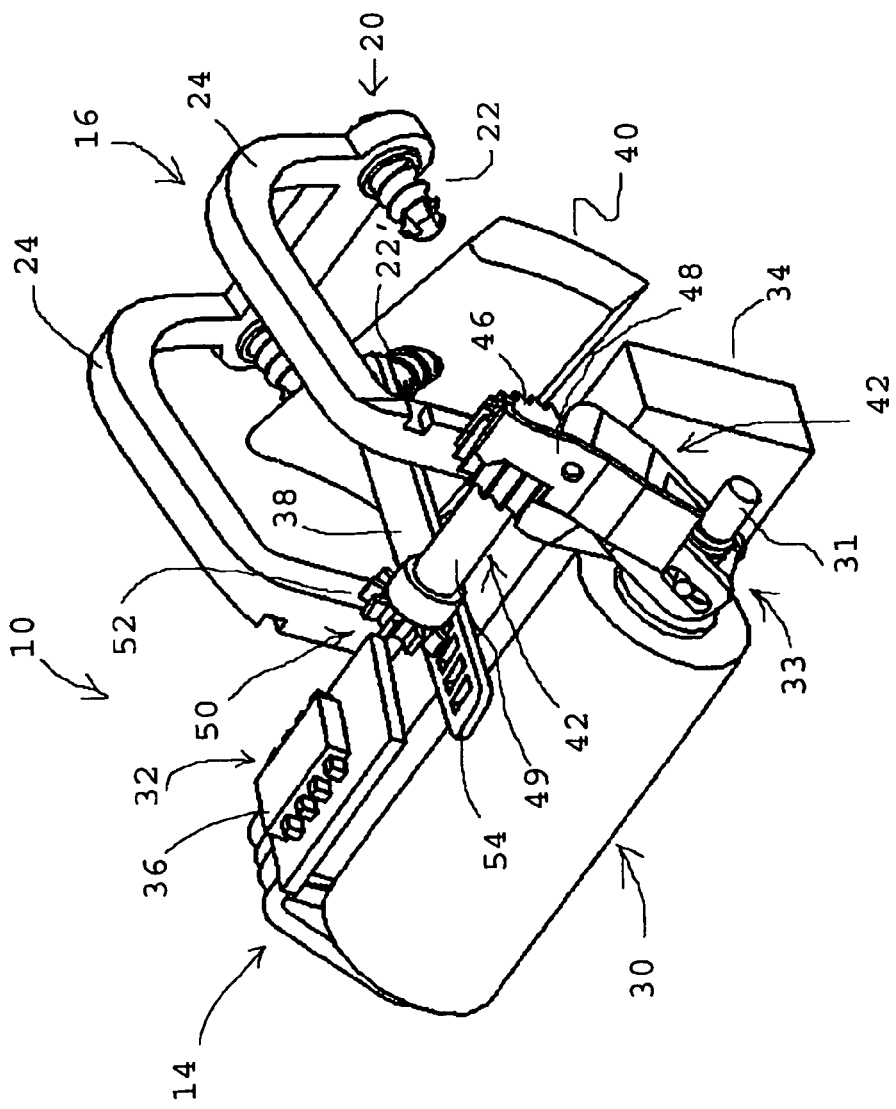
FIG. 5 is a perspective view of the embodiment of FIGS. 1, 3 and 4 absent an outer casing or housing.
Figure 6:
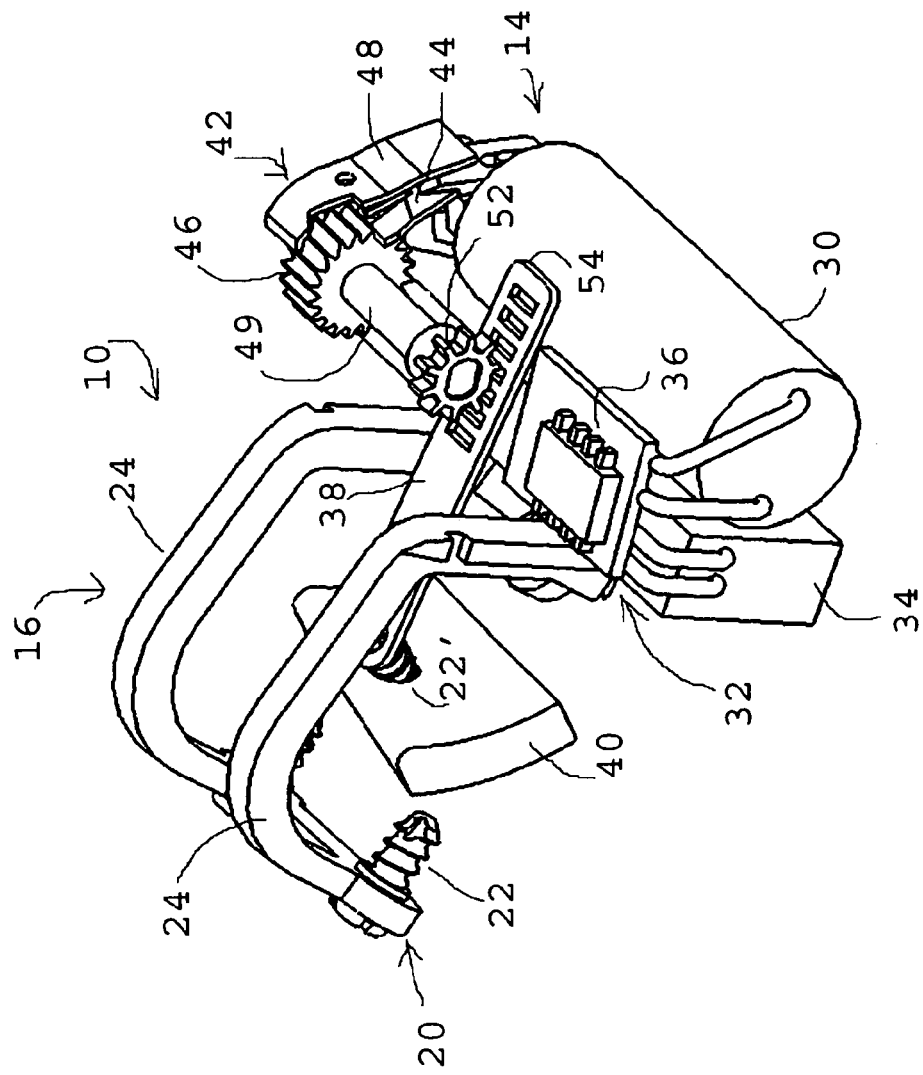
FIG. 6 is a perspective view of the embodiment of FIG. 5.

More specifically and with primary reference to FIGS. 1 and 3-7, one preferred embodiment of the distraction assembly generally indicated as 10 comprises a housing 12 disposed and structured to enclose and at least partially protect a drive assembly generally indicated as 14 in FIGS. 5 and 6. In addition, a support frame generally indicated as 16 is connected in supporting relation to the housing 12 and enclosed drive assembly 14. Accordingly, an intended anchored placement of the drive assembly 12 is assured in relation to a corresponding bone tissue 18. In the various Figures presented herewith, the bone tissue is schematically represented as the mandible. However, it is emphasized that other bone tissue portions within the mouth of the patient can serve as an anchoring base, other than the mandible.

Further, the operative disposition of the distraction assembly 10 may therefore be further described as locating the housing 12 and drive assembly 14 on a buccal side of the bone tissue or mandible 18. As such, the support frame 16 includes an outer or distal portion 20 secured to the lingual side of the bone tissue 18 by anchoring screws or other appropriate anchoring connectors or members 22. As also represented throughout the Figures, the support frame 16 includes at least one, but preferably a plurality elongated arms 24 disposed in spaced relation to one another and extending from the distal or outer portion 20 to an inner or proximal portion 20' of the support frame 16. Also, the inner portion 20' is connected to or otherwise supportively associated with the housing 12 and drive assembly 14. Moreover, the one or more arms 24 defining at least a portion of the support frame 16 are disposed to overly and be spaced from what may be generally referred to as the implant site 26. Further, the implant site may be further defined by adjacently located spaced apart teeth of the patient schematically represented as 28 and 29 in FIG. 3.

Figure 7:
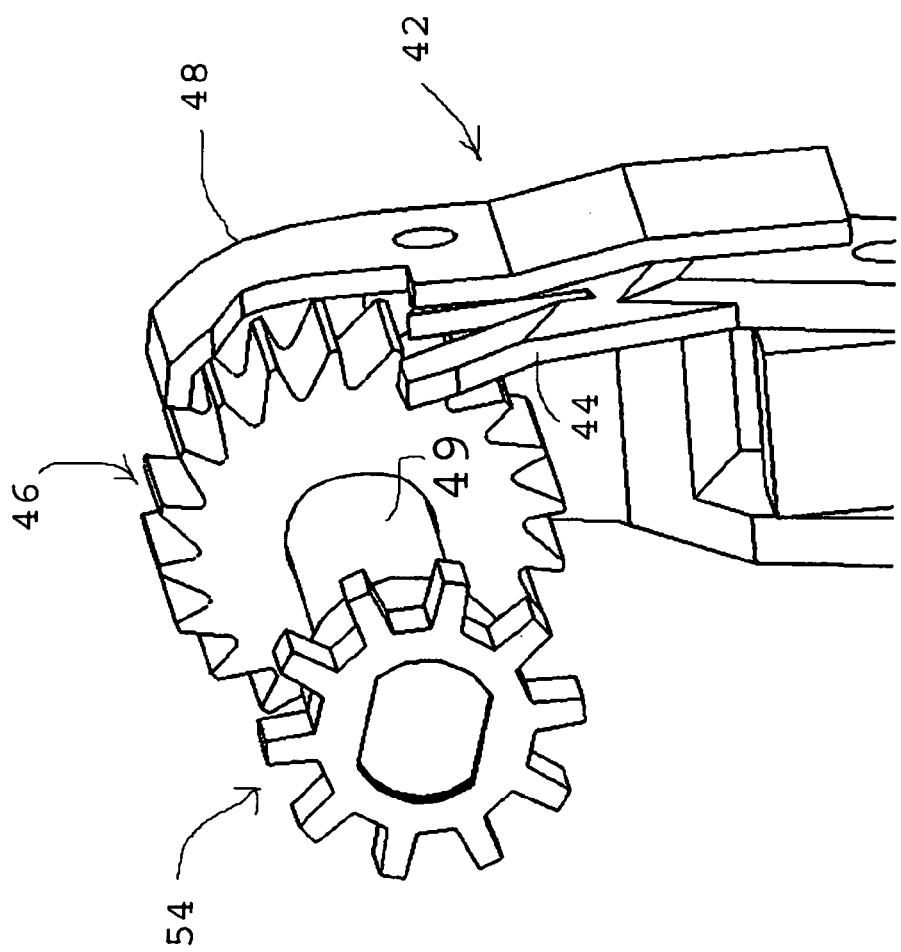
FIG. 7 is a perspective, detailed view in partial cutaway of an indexing assembly associated with the preferred embodiment of FIGS. 1 and 3-6.
Figure 8:
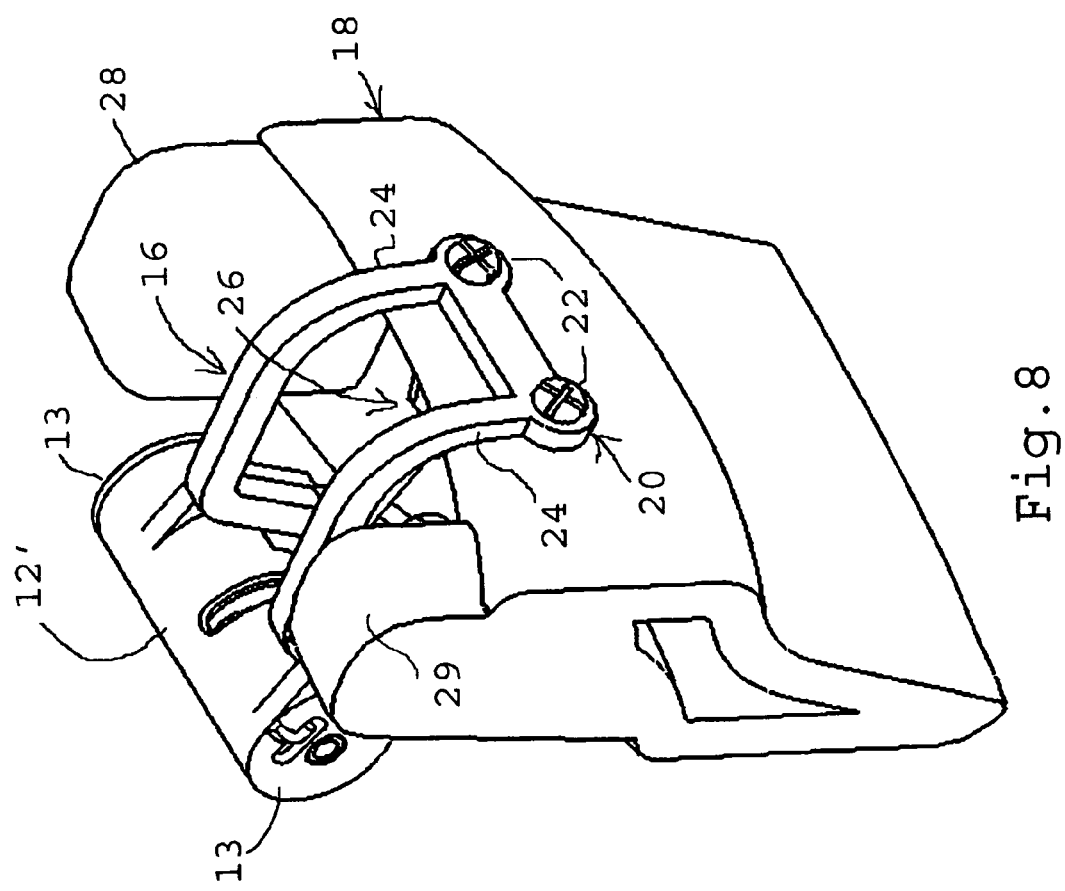
FIG. 8 is a perspective view of the preferred embodiment of FIG. 2 mounted within an oral cavity of the patient in an operative position relative to an implant site.
Figure 9:
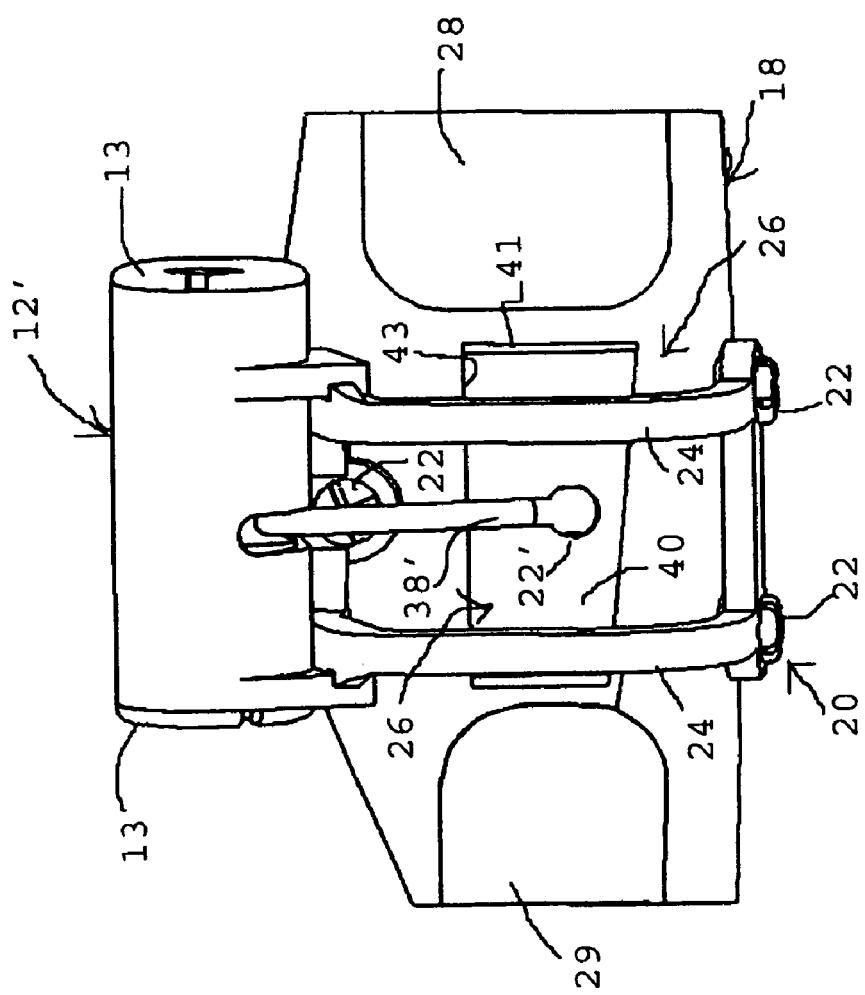
FIG. 9 is a top view of the embodiment of FIG. 8.
Figure 10:
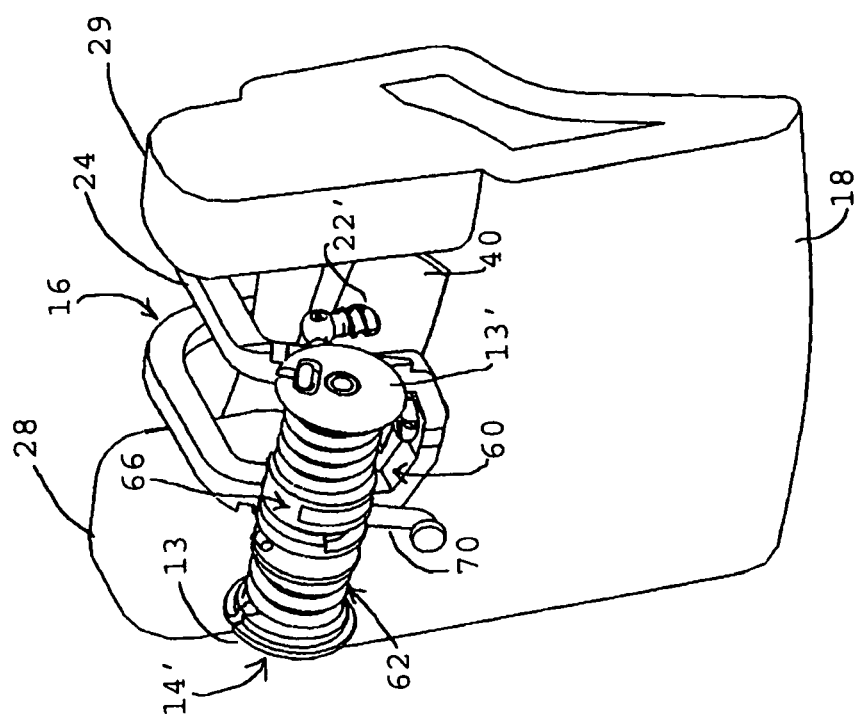
FIG. 10 is an opposite perspective view of the embodiment of FIG. 8 absent an outer housing.
Figure 11:
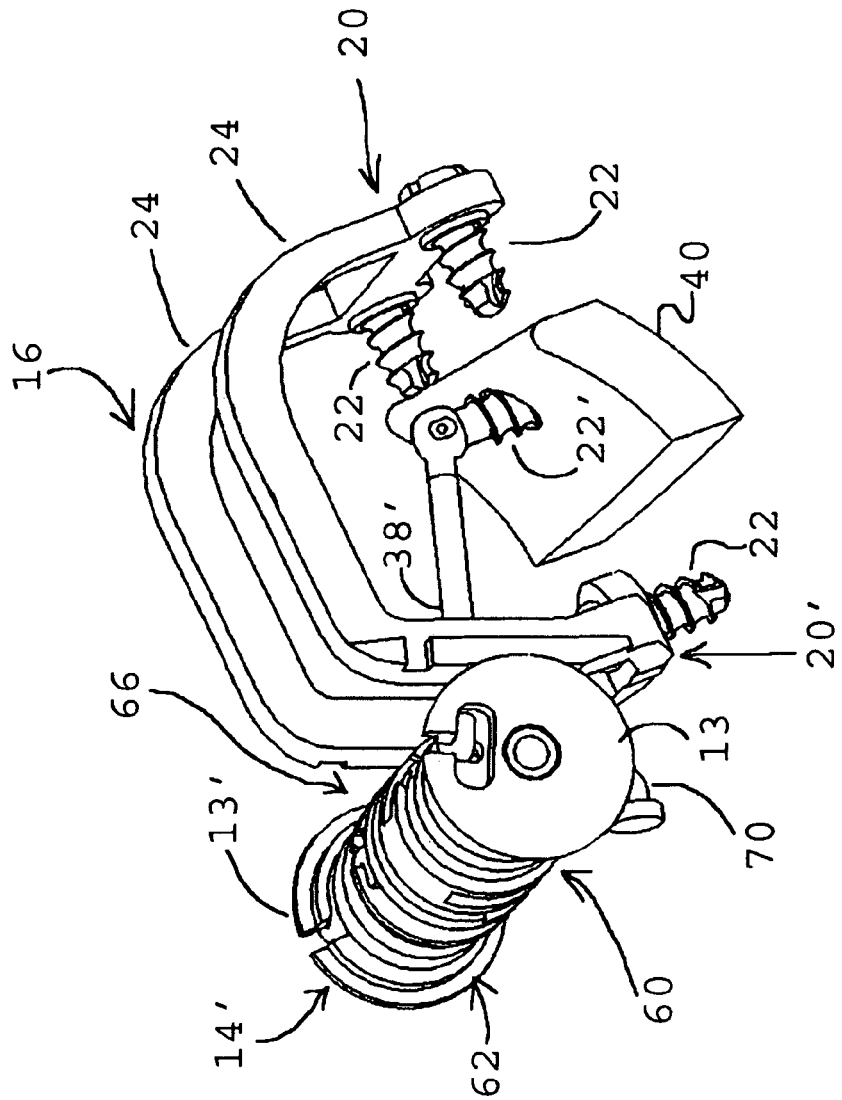
FIG. 11 is a perspective view of the preferred embodiment of FIGS. 2, 8, 9 and 10 absent an outer housing or casing and unattached directly at an implant site.
Figure 12:
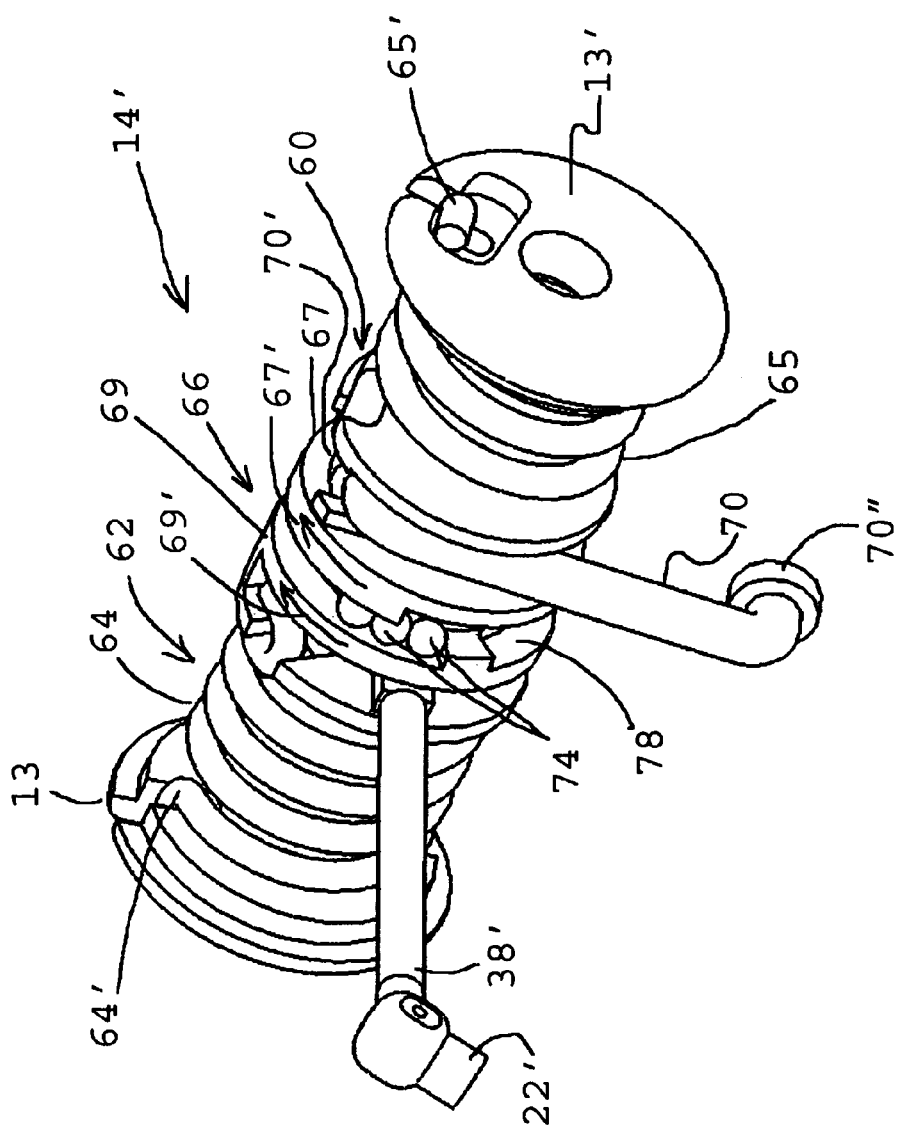
FIG. 12 is a perspective view of interior, working components of the preferred embodiment of FIGS. 2 and 8-11.

With primary reference to FIGS. 5-7, the distraction assembly 10 includes the drive assembly 14 including a drive component generally defined by an electric drive motor 30 and a timing assembly 32 generally defined by an electronic control 36. The drive motor 30 may be powered by electrical energy delivered under a controlled or regulated basis from an appropriate battery or other electrical power source. The battery (not shown for purposes of clarity) may be mounted within the housing or casing 12 or otherwise cooperatively structured as within interior component 34. In addition, the timing assembly 32 comprises the electronic control 36 which is disposed and structured to regulate or restrict the flow of current from the battery 34 to the electric drive motor 30 on a pulsed, sequenced or otherwise periodic basis. As such, the controlled delivery of current flow to the electric motor 30 accomplishes the intended incremental displacement of a bone segment 40 associated with the implant site 26, as will be explained in greater detail hereinafter.

Additional structural features of this embodiment of the deflection assembly 10 include at least one displacement member 38 disposed in driven relation to the driving assembly 14. As represented throughout FIGS. 1 and 3-7, the at least one displacement member 38 has an elongated configuration and a proximal or outer portion connected to the bone segment 40, which is to be displaced to facilitate the generation of bone growth at the implant site 26. Secure connection between the outer portion of the displacement member 38 and the bone segment 40 can be accomplished by an anchoring screw or any other appropriate connector 22'.

In order to properly drive and therefore incrementally advance the one displacement member 38, the drive assembly 14 and in particular the drive component or electric motor 30 is drivingly connected to an indexing assembly 42 represented in detail in FIG. 7. The indexing assembly 42 includes a ratchet assembly comprising a first drive component 44 disposed in driving relation with each of the plurality of teeth associated with a timing gear 46. In addition, the ratchet assembly 42 includes a ratchet member 48 which is disposed and structured in cooperative relation to the teeth of the timing gear 46 so as to assure an accurate, incremental advancement of the timing gear 46 and prevent any inadvertent reverse travel of the timing gear 46. As such, the ratchet member 48 serves as a true ratchet device assuring the incremental advancement of the timing gear 46 and accordingly the displacement member 38 in an accurate, reliable and intended fashion.

The drive component 44 is connected in driven relation to the output 31 of the electric motor 30, wherein the drive component is defined by appropriate drive linkage 33. In addition, the indexing assembly 42 further comprises a drive linkage including an elongated drive shaft 49 as well as a rack and pinion assembly generally indicated as 50. The rack and pinion assembly 50 includes a pinion gear 52 and a rack gear 54 movably interconnected in meshing engagement with one another. As also noted, the rack gear 54 is integrally formed with or otherwise fixedly connected to the displacement member 38 such that interaction between the pinion gear 52 and the rack gear 54 will cause movement of the displacement member 38 along its predetermined path of travel. In turn, such forced or driven movement of the displacement member 38 causes a concurrent displacement of the bone segment 40 relative to the implant site 26.

As set forth above, one feature of the distraction assembly 10 is the structuring of the drive assembly 14 to include a cooperative, preferably interactive operation of the drive component or electric motor 30 and the timing assembly 32 in the form of the electronic control 36. Such interactive operation is such as to accomplish an incremental advancement of the displacement member 38 which in turn results in a concurrent, incremental displacement of the bone segment 40 relative to the implant site 26. Required bone regeneration will thereby be effectively automated and occur at a predetermined and preferably constant rate.

Operation of the distraction assembly 10 comprises the timing assembly 32 and more specifically the electronic control 36 regulating current flow to the drive component or electric motor 30. As such, the electronic control 36 includes appropriate electronic circuitry or other electronic structuring operative to deliver a regulated pulsed or periodic current flow to the electric drive motor 30. Such regulated current flow will cause a periodic operation or activation of the electric motor 30 which in turn will cause the same periodic or incremental rotation or other driving movement of the power take-off 31 connected to the electric drive motor 30 and moveable therewith. The periodic powering and movement of the power take-off 31 will cause the same periodic advancement of the drive component 34 interacting with the individual teeth of the timing gear 46. As such, the timing gear 46 will be incrementally advanced which results in the same incremental rotation of the drive shaft 49 and fixedly attached pinion gear 52. Incremental rotation of the pinion gear 52 will result in an incremental advancement of the displacement member 38 in a substantially linear or laterally directed path of travel as schematically represented by the directional arrow 55 in FIGS. 4, 16 and 17.

As such, the displacement member 38 can be said to be incrementally advanced along a predetermined path of travel, schematically indicated by directional arrow 55, which in turn will cause a concurrent, incremental displacement of the bone segment 40, which is fixedly secured to the distal portion of the displacement member 38 by anchoring screw or like connector 22'. For purposes of clarity the incremental advancement of the bone segment 40 relative to the implant site 26, in accordance with the structure and operation of the distraction assembly 10 of FIGS. 1 and 3-7, is schematically represented in FIGS. 16 and 17. More specifically, FIGS. 16 and 17 represent a cross sectional schematic view of corresponding bone tissue 18 more specifically in the form of the alveolar ridge, which is typical in patients that have lost molars. The objective, in order to accomplish an effective dental implant, is to create sufficient bone mass at the top of the ridge or bone tissue 18 that would allow the anchoring of implants that can be as much as 3 mm in girth. For this size implant, a minimum of 4 mm ridge is desirable. Accordingly, the formation of the displaceable bone segment 40 is accomplished by forming a window 41 cut into the top of the ridge of the bone tissue 18 using appropriate dental instrumentation. Bone segment 40 is then at least separated or partially fractured to form the segment 40 in a manner which establishes a hinged connection as at 43. The hinged connection facilitates displacement of the bone segment 40 while maintaining a sufficient vascular network which will continue to feed the bone segment 40 and the associated bone tissue 18 throughout the distraction process.

Accordingly, the distraction assembly 10 when operated will cause the predetermined, incremental advancement of the displacement member 38 along a predetermined, substantially linear or laterally directed path of travel 55. This incremental advancement of the displacement member 38 will cause a forced movement of the anchoring member 22' which in turn causes a somewhat hinged or pivotal displacement of the bone segment 40 also on an incremental basis. Therefore, as represented schematically in FIGS. 16 and 17 upon instigation of the operation of the drive component or electric motor 30, the displacement member 38 will begin, over a predetermined period of time, to incrementally travel along the predetermined path of travel 55 causing movement of the anchor member 22' and the pivotal or hinged incremental displacement of the bone segment 40 in the manner which should be apparent from a comparative view of FIGS. 16 and 17.

As will be explained hereinafter, the application and operation of the additional preferred embodiment of the distraction assembly 10', as represented in FIGS. 2 and 8-15 results in a predetermined path of travel 55' having an at least partially and substantially arcuate configuration as also indicated in FIGS. 16 and 17. Regardless of the specific directional configuration of the path of travel 55 or 55' of the displacement member 38 or 38' the bone segment 40 will be incrementally displaced at a predetermined and preferably constant rate by virtue of the hinged or pivotal connection 43 and its formation from the defined window 41 formed in the bone tissue 18.

Further with regard to FIGS. 16 and 17, it should be noted that regenerated bone mass would be filling the area adjacent to or associated with the window 41, wherein such regenerated bone mass is not shown for purposes of clarity.

With reference to the additional preferred embodiment of the distraction assembly 10' as represented in FIGS. 2 and 8-12, similar structural and operative features exist between the two preferred embodiments 10 and 10' of the distraction assembly. More specifically, the support frame 16 is interconnected to the mandible or other corresponding bone tissue 18 such that is it anchored to both the lingual and buccal sides thereof. As set forth above with the embodiment of FIG. 1, the distraction assembly 10' includes a casing 12' structured to house and/or at least partially enclose a drive assembly 14'. As with the embodiment of FIG. 1, the operative disposition of the distraction assembly 10', of the embodiment of FIGS. 2 and 8-15 may be further described as locating the housing 12' and drive assembly 14' on a buccal side of the bone tissue or mandible 18. As such, the support frame 16 includes the outer or distal portion 20 secured to the lingual side of the bone tissue 18 by anchoring screws or other appropriate anchoring connectors or members 22. As also represented, the support frame 16 includes at least one, but preferably a plurality elongated arms 24 disposed in spaced relation to one another and extending from the distal or outer portion 20, connected to the lingual side of the bone tissue 18 to an inner or proximal portion 20' of the support frame 16, connected to the buccal side of the bone tissue 18. Also, the inner portion 20' is connected to or otherwise supportively associated with the housing 12' and drive assembly 14'. Moreover, the one or more arms 24 defining at least a portion of the support frame 16 are disposed to overly and be spaced from what may be generally referred to as the implant site 26. Further, the implant site 26 may be further defined by adjacently located, spaced apart teeth of the patient schematically represented as 28 and 29 in FIGS. 8-10.

Additional features of the embodiment of FIGS. 2 and 8-15 of the distraction assembly 10' include a displacement member 38' connected in driven relation to the drive assembly 14' such that the displacement member 38' is incrementally advanced along a predetermined path of travel 55'. Such an incremental advancement of the displacement member 38' in turn will cause a concurrent, incremental displacement of the bone segment 40, due to its attachment to the distal or outer portion of the displacement member 38' by an anchoring screw 22' or other appropriate connector.

As represented in FIGS. 16 and 17 described above, a distinguishing feature of the operation and structural components of the distraction assembly 10', as versus at the distraction assembly 10, is the establishment of a predetermined path of travel 55' of the displacement member 38' having an at least partially and substantially arcuate or curvilinear configuration as schematically represented. Such an arcuate or at least partially curvilinear configuration of the predetermined path of travel 55', of the displacement member 38' will cause the intended incremental displacement of the bone segment 40 about the hinged junction or portion 43, connecting the bone segment to the adjacent or contiguous part of the bone tissue. As such, the bone segment 40 will be incrementally displaced in a hinged or pivotal fashion, as explained above with specific reference to the embodiment of FIGS. 1 and 3-7.

Additional structural and operative features of the distraction assembly 10' include the drive assembly 14' comprising a timing assembly generally indicated as 60 and a drive component generally indicated as 62 as represented in FIGS. 10-15. More specifically, the drive component 62 comprises a first biasing assembly 64 which may include, but not be limited to, a torsion spring or other similarly functional member(s). One end 64' of the biasing assembly 64 is secured to an end plate or disk structure 13. The end plate or disk 13 is fixedly connected to, fixedly disposed within or otherwise comprises a fixed part of the housing 12'. As such, the disk 13 is fixed and thereby serves to anchor or maintain the corresponding end 64' of the biasing assembly 64 in a fixed position. The opposite end 64" of the biasing assembly 64 is connected to a release mechanism generally indicated as 66 which will be described in greater detail hereinafter. In addition, the displacement member 38' is also connected to or otherwise associated with the release assembly 66, so as to at least partially move therewith. As such, the biasing assembly 64 is interconnected in biasing, substantially driving relation to the displacement member 38' such that the displacement member 38' will be incrementally advanced, as will be explained in greater detail with specific reference to FIGS. 13-15. As represented in these figures, the release assembly 66 includes structural and operative features which regulate or restrict movement of the displacement member 38' even while the biasing or driving force is exerted thereon by the biasing assembly 64. Further, the release assembly 66 is also connected to the timing assembly 62. Cooperative operation and structuring between the release assembly 66, the timing assembly 60 and the drive component 62 of the drive assembly 14' is such as to reliably accomplish the intended incremental advancement or travel of the displacement member 38', which in turn results in the incremental displacement of the bone segment 40 about the hinged connection 43 at the implant site 26.

The timing assembly 60 is cooperatively disposed and structured so as to interactively operate with the drive component 62 and biasing assembly 64 by regulating its movement, thereby regulating the movement or advancement of the displacement member 38' along its intended, arcuate path of travel 55'. Accordingly, the timing assembly 60 comprises a timing member 70 which is represented as having an elongated configuration, but which may be otherwise structured and configured so as to effectively influence the movement and operation of the release assembly 66 and therefore the movement of the of the biasing component 64 as well as the periodic advancement of the interconnected displacement member 38'.

Additional structural and operative details of the timing assembly 60 include the provision of a biasing member 65 having one end 65' connected to a fixed disk or plate 13', oppositely disposed to the disk 13, but similarly anchored or fixedly secured to or within the housing 12'. The biasing member 65 includes its opposite end as at 65" connected to or otherwise operatively associated with the release assembly 66. As such, the biasing member 65 is disposed and structured to exert a substantially continuous biasing force on the release assembly 66 and accordingly the timing member 70. By virtue of the fact that the timing member 70 is connected to or otherwise associated with the release assembly 66, as at 70', the biasing force exerted on the release assembly 66 is transferred, at least in part, to the timing member 70 thereby exerting a predetermined stress or biasing force thereon. Of further note is that the opposite end 70", or other appropriate portion of the timing member 70, is fixedly disposed on the interior of the housing or casing 12'. Accordingly, the "position" of the timing member 70 is not intended to change because of the biasing force exerted thereon by the biasing member 65. However, the timing member 70 is intended to be "deformed" in terms of demonstrating predetermined "creep" characteristics as described above and as further explained in greater detail with regard to the intended operation of the self contained drive assembly 14'.

More specifically, the timing member 70 is preferably formed of a material which demonstrates predetermined "creep" characteristics. As set forth herein, the term "creep" is used to describe the tendency of a material to be "deformed" in reaction to stresses or forces applied thereto. With specific reference to the material from which the timing member 70 is formed, it is known that under given pressure and temperature, some materials undergo the aforementioned "creep" or plastic deformation. The timing member 70 will be exposed to a fairly constant temperature 98.6° F. when mounted within the mouth of a patient for a relatively extended period of time. In that the timing member 70 is interconnected to the biasing member 65, preferably through the release assembly 66, a continuous biasing force, tension or stress will be applied to the timing member 70. As a result, a lengthening or other predetermined deformation of the timing member 70 will occur due to its predetermined creep characteristics, wherein such deformation can be predicted and determined. The timing member 70 thereby serves to regulate, control or otherwise restrict the movement of the release assembly 66, which in turn regulates the periodic advancement of the displacement member 38' due to its connection or other appropriate structuring with the release assembly 66.

Structural and operative details of the release assembly 66 are primarily represented in FIGS. 12-15. The release assembly 66 is interconnected between the timing assembly 60 and the drive component 62 by virtue of it being connected to substantially corresponding opposite ends 64" and 65" of the biasing assembly 64 and the biasing member 65. For purposes of clarity, the displacement member 38' is not represented in FIGS. 13-15. However, as clearly demonstrated in FIG. 12 the displacement member 38' as well as the timing member 70 are both connected, attached or otherwise operatively associated with the release assembly 66 so as to at least partially move therewith. Additional operative and structural features of the release assembly 66 include it comprising movably interconnected release segments 67 and 69. Moreover, the release segments 67 and 69 are movably and more specifically rotationally connected to one another, such that each of the release segments 67 and 69 will travel or rotate in the same direction, as schematically indicated by directional arrows 67' and 69'. The rotation of each of the release of the segments 67 and 69 is due, at least in part, to biasing forces being exerted thereon respectively by the biasing member 65 and the biasing assembly 64.

However, the release assembly 66 further comprises a release mechanism generally indicated as 72 and at least partially defined by a plurality of balls or like release members 74 initially disposed within an upper or first track or raceway 75 disposed between and at least partially defined by the adjacent but spaced apart portions of the release segments 67 and 69. Further, a stop member 76 is disposed within or otherwise associated with the raceway or track 75 in a position which serves to restrict movement of the release balls or members 74. As such, the plurality of release members or balls 74 are "trapped" or otherwise at least initially maintained within the track 75. Further, the release members 74 are cooperatively disposed and structured with the release segments 67 and 69, so as to regulate the movement there between in a manner which assures the intended predetermined, incremental advancement of the displacement member 38'. As set forth above, such predetermined incremental advancement of the displacement member 38' will result in an incremental displacement of the bone segment 40 about the hinged connection 43 by virtue of the bone segment 40 being attached to the outer end of the displacement member 38', as at 22'.

Figure 13:
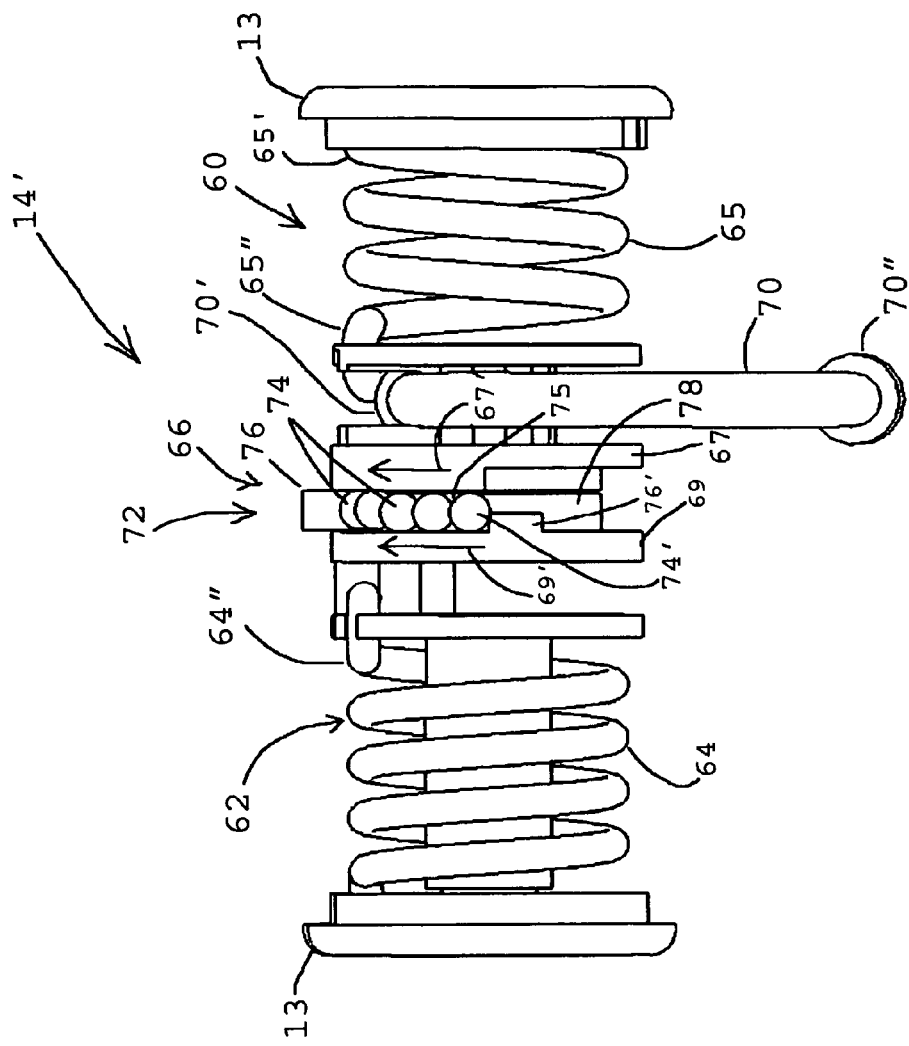
FIGS. 13 through 15 are sequential operative positions of the interior working components of the preferred embodiment of FIGS. 2 and 8-12.
Figure 14:
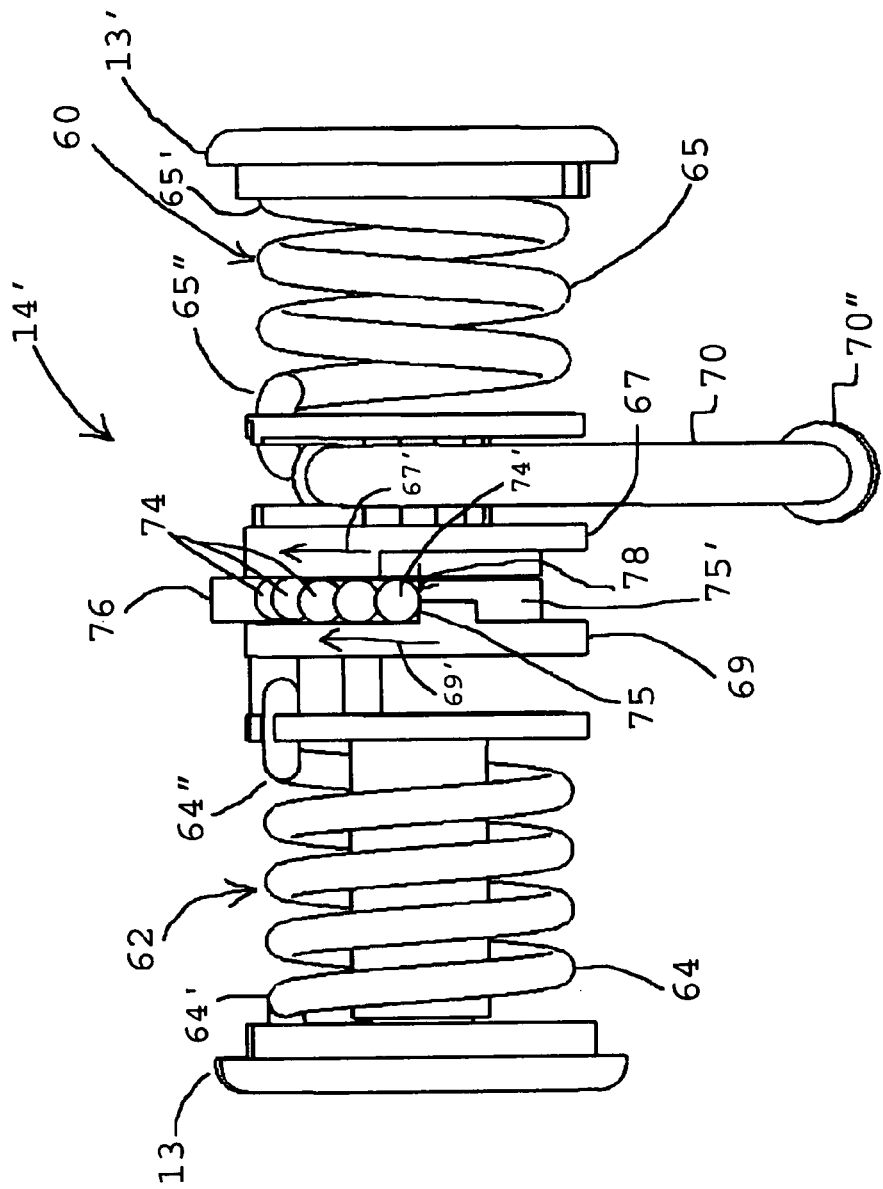
Figure 15:
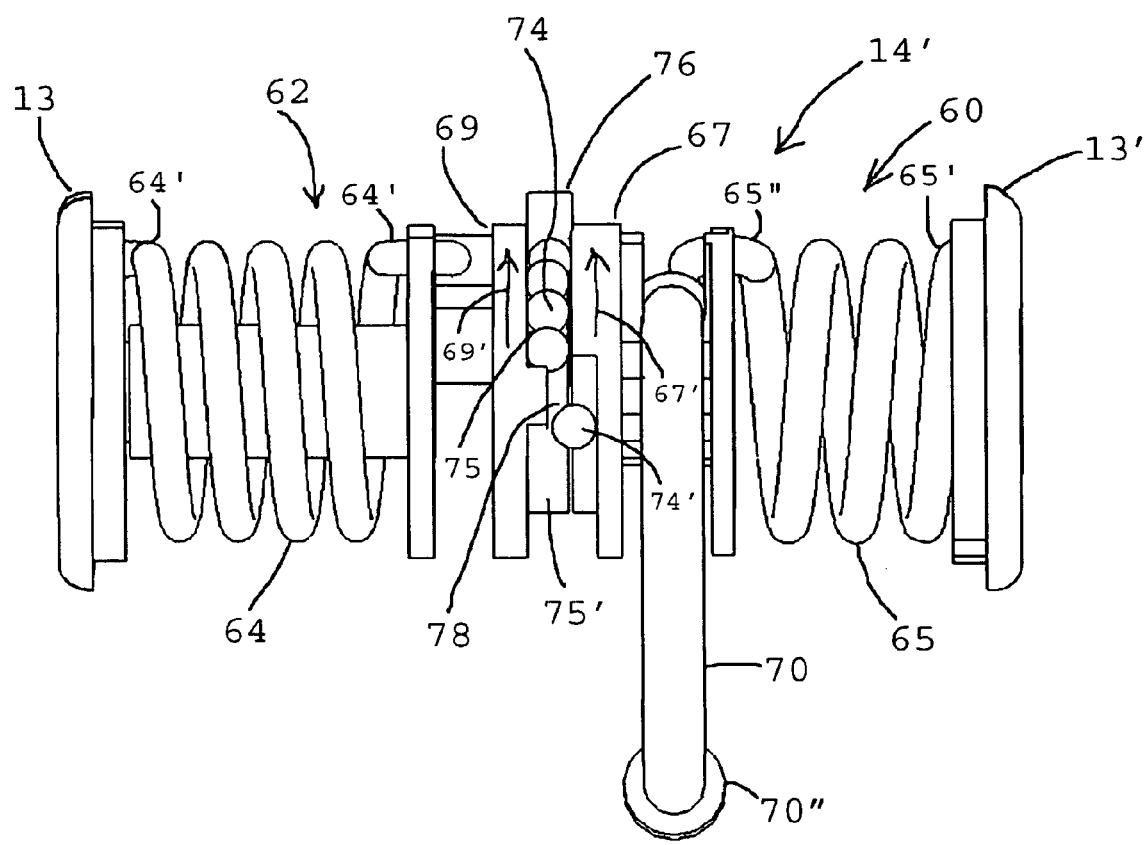

As sequentially demonstrated in the relative positions of the release segments 67 and 69 in FIGS. 13-15, the self contained drive assembly 14' accomplishes an incremental advancement of the displacement member 38' (see FIG. 12) due to the predetermined creep characteristics of the material from which the timing member 70 is formed. More specifically, the biasing member 65 places a substantially constant biasing force or stress on the timing member 70. In that the timing member 70 is formed from a material demonstrating the aforementioned predetermined creep characteristics, it will periodically "deform" or, in the case of the elongated timing member 70, will elongate at a substantially constant rate assuming that the biasing force or stress placed thereon is sufficient and maintained. Therefore, the timing member 70 will be periodically elongated or otherwise deformed resulting in a movement or rotation, as at 67' of the release segment 67 in the direction indicated.

As represented in FIG. 13, release segment 69 is restricted or prevented from moving relative to release segment 67 due to the fact that the balls or release members 74 are trapped between the stop member 76 and an oppositely disposed stop member 76' connected to the release segment 69. However, due to the aforementioned creep characteristics of the timing member 70 and the stress or biasing force placed thereon by biasing member 65, the timing member 70 will eventually and periodically be deformed or elongated. This deformation or "creep" of the timing member 70 will result in a first incremental movement of the release segment 67, as schematically demonstrated by directional arrow 67'. When the release segment 67 has rotated or otherwise traveled a sufficient distance, as demonstrated in FIG. 14, the end most release ball or member 74' will pass through an opening 78 disposed adjacent the stop member 76' and between the release segments 67 and 69.

As demonstrated in FIG. 15 the release ball or member 74 will then pass into a next adjacent raceway or track 75'. As a result, the release segment 69 will be allowed to "follow" or rotate, as schematically represented by the directional arrow 69', until the stop member 76' is forced into movement restricting engagement with the next, endmost release ball or member 74', as initially represented in FIG. 13. As such the distance of the incremental travel of the release segment 69 will substantially correspond to the size of the release ball(s) 74. As a result of the incremental rotation or advancement of the release segment 69, the displacement member 38', being connected to and movable with the release segment 69 (see FIG. 12), will be incrementally advanced, thereby resulting in the incremental displacement of the bone segment 40 relative to the bone tissue 18. As the timing member 70 continues to be periodically deformed and/or elongated, the release segments 67 and 69 will be incrementally rotated into a location where the next release ball or member 74 is allowed to pass through the opening 78. This will result in the successive, periodic, incremental rotation or travel of the release segment 69 and corresponding incremental advancement of the displacement member 38', normally until all the release balls or members 74 have been removed from their trapped or movement restricting position within track or raceway 75, between the stop members 76 and 76'.

Accordingly, the self contained drive assembly 14' includes the timing assembly 60 and the drive component 62, which are cooperatively structured and interactively operable to cause the incremental advancement of the displacement member 38' and accordingly, the concurrent incremental displacement of the bone segment 40 relative to the implant site 26. Due to the fact that a substantially continuous biasing force is exerted on the release segment 67 of the release assembly 66, a continuous stress will be exerted on the timing member 70. In that the timing member 70 is formed of a material structured to demonstrate the aforementioned, predetermined creep characteristics, the timing member 70 will be constantly stretched, elongated or otherwise "deformed" on an ongoing basis. This will result in a periodic rotation and/or incremental advancement of the release segment 67. Because the biasing assembly 64 also exerts a substantially continuous biasing force on the release segment 69, it will be periodically and incrementally rotated upon release of a next, endmost release ball or member 74 through the opening 78. A corresponding incremental advancement of the displacement member 38' along its curvilinear or at least partially arcuate path of travel 55' will thereby occur due to it being connected to and movable with the release segment 69.

Accordingly, due to the inherent interactive operation of the timing assembly 60 and the drive component 62, the drive assembly 14' is said to be "self contained" by virtue of the fact that no external or supplementary energy or power need be delivered to the drive assembly 14' in order to cause its operation or activation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A distraction assembly structured to automatically facilitate bone growth for the application of a dental implant, said distraction assembly comprising:
   a self-contained, autonomous drive assembly including a drive motor, said drive assembly dimensioned and configured for operative placement within the mouth of a patient,
   a support frame connected in supporting relation to said drive assembly and anchored to a correspondingly disposed bone tissue within the mouth,
   at least one displacement member securable to a predetermined bone segment associated with an implant site,
   said one displacement member connected in driven relation to said drive assembly and movable along a predetermined path of travel concurrent to displacement of the bone segment secured thereto,
   an indexing assembly connected in driving relation to said one displacement member and in driven relation to said drive motor, and
   said drive assembly comprising a timing assembly cooperatively structured with a remainder of said drive assembly to automatically cause incremental advancement of said displacement member along said predetermined path of travel and displacement of the bone segment relative to said implant site.

2. A distraction assembly as recited in claim 1 wherein said indexing assembly includes mechanical linkage driven by said drive motor and disposed in driving relation to said one displacement member.

3. A distraction assembly as recited in claim 1 wherein said drive motor is electrically powered and disposed in driving relation to said one displacement member via said indexing assembly.

4. A distraction assembly as recited in claim 1 wherein said indexing assembly comprises a ratchet assembly and drive linkage, said ratchet assembly connected in driven relation to said drive motor, said drive linkage interconnected in driven relation to said ratchet assembly and in driving relation to said one displacement member.

5. A distraction assembly as recited in claim 4 wherein said drive linkage comprises a timing gear operatively connected to said indexing assembly and an interconnecting gear assembly disposed in driven relation to said timing gear and in driving relation to said one displacement member.

6. A distraction assembly as recited in claim 5 wherein said interconnecting gear assembly includes a rack and pinion assembly including a pinion gear connected in driving relation to said rack gear, said rack gear connected in driving relation to said one displacement member.

7. A distraction assembly as recited in claim 4 wherein said timing assembly comprises an electronic control disposed and structured to periodically activate said drive motor and regulate current flow thereto to establish a substantially predetermined rate of incremental advancement of said one displacement member along said predetermined path of travel.

8. A distraction assembly as recited in claim 3 wherein said indexing assembly comprises a ratchet assembly and drive linkage, said ratchet assembly connected in driven relation to said drive motor, said drive linkage interconnected in driven relation to said ratchet assembly and in driving relation to said one displacement member.

9. A distraction assembly as recited in claim 1 wherein said one displacement member comprises an elongated configuration including a distal portion connected to the bone segment and a proximal portion interconnected to said drive assembly.

10. A distraction assembly as recited in claim 9 wherein said predetermined path of travel is substantially linear.

11. A distraction assembly as recited in claim 10 wherein said one displacement member and said drive assembly are cooperatively structured to facilitate an incremental, hinged displacement of the bone segment and a substantially constant rate of distraction.

12. A distraction assembly as recited in claim 1 wherein said support frame is at least partially disposed in spaced, overlying relation to the implant site and includes an anchoring assembly secured to correspondingly disposed bone tissue.

13. A distraction assembly as recited in claim 12 wherein said anchoring assembly comprises a first and second anchor structures respectively disposed adjacent a distal portion and a proximal portion of said support frame.

14. A distraction assembly as recited in claim 13 wherein said first and second anchor structures are relatively disposed to connect said support frame to a lingual portion and a buccal portion of the corresponding bone tissue.

15. A distraction assembly as recited in claim 13 wherein said drive assembly is disposed adjacent said proximal portion of said support frame corresponding to a buccal portion of the bone tissue.

16. A distraction assembly as recited in claim 1 wherein said self contained drive assembly is interconnected in driving relation to said one displacement member, said self contained drive assembly structured to facilitate automatic, incremental advancement of said one displacement member and concurrent, incremental displacement of the bone segment.

17. A distraction assembly structured to facilitate bone growth for the application of a dental implant, said distraction assembly comprising:

a self-contained drive assembly including a drive motor, said self contained drive assembly dimensioned and configured to be completely disposed within the mouth of the patient at least during the distraction process, a support frame connected in supporting relation to said drive assembly and anchored to a correspondingly disposed bone tissue within the mouth, at least one displacement member secured to a bone segment associated with an implant site, an indexing assembly connected in driving relation to said one displacement member and in driven relation to said drive motor, and said drive assembly comprising a timing assembly, said timing assembly interactively operable with said drive motor to automatically cause incremental advancement of said one displacement member and concurrent displacement of the secured bone segment relative to the implant site.

18. A distraction assembly as recited in claim 17 wherein said timing assembly is connected in movement restricting relation to said drive component; said timing assembly structured to determine incremental movement of said drive component.

19. A distraction assembly as recited in claim 17 wherein said drive motor comprises an electric drive motor and said timing assembly comprises an electronic control structured to regulate current flow to said electric motor.

20. A distraction assembly as recited in claim 19 wherein said electric drive motor and said electronic control are cooperatively structured to establish a predetermined rate of incremental advancement of said one displacement member along said predetermined path of travel.

21. A distraction assembly as recited in claim 20 wherein said predetermined path of travel of said one displacement member at least partially comprises a substantially linear configuration.

22. A distraction assembly as recited in claim 17 wherein said drive assembly is disposed on said support frame adjacent a buccal portion of the bone tissue within the mouth.

23. A distraction assembly structured to automatically facilitate bone growth for the application of a dental implant, said distraction assembly comprising:

a drive assembly including a drive motor, said drive assembly dimensioned and configured for operative placement within the mouth of a patient, a support frame connected in supporting relation to said drive assembly and anchored to a correspondingly disposed bone tissue within the mouth, at least one displacement member securable to a predetermined bone segment associated with an implant site and movable along a predetermined path of travel concurrent to displacement of the bone segment secured thereto, an indexing assembly connected in driving relation to said one displacement member and in driven relation to said drive motor, and said drive assembly comprising a timing assembly cooperatively structured with a remainder of said drive assembly to cause incremental advancement of said displacement member along said predetermined path of travel and displacement of the bone segment relative to said implant site independent of a driving engagement from a position external to the mouth of the patient.

* * * * *